(12) United States Patent
Carrasco et al.

(10) Patent No.: US 8,575,855 B2
(45) Date of Patent: Nov. 5, 2013

(54) HOLLOW CATHODE LAMP ELAPSED TIME RECORDING SYSTEM

(75) Inventors: Sunita Carrasco, Danbury, CT (US); David Hager, Norwalk, CT (US); Tack-Boon Yee, Singapore (SG)

(73) Assignees: PerkinElmer Health Sciences, Inc., Waltham, MA (US); PerkinElmer Singapore Pte. Ltd., Singapore (SG)

( * ) Notice: Subject to any disclaimer, the term of this patent is extended or adjusted under 35 U.S.C. 154(b) by 321 days.

(21) Appl. No.: 12/982,749

(22) Filed: Dec. 30, 2010

(65) Prior Publication Data

US 2012/0169237 A1 Jul. 5, 2012

(51) Int. Cl.
*H01J 17/06* (2006.01)
(52) U.S. Cl.
USPC ............ 315/291; 315/307; 313/618; 313/632
(58) Field of Classification Search
USPC .................. 313/618, 631, 632; 356/328, 326; 315/291, 307, 308, 56
See application file for complete search history.

(56) References Cited

U.S. PATENT DOCUMENTS

| | | | |
|---|---|---|---|
| 4,698,550 A | 10/1987 | Kobayashi et al. | 313/618 |
| 5,861,949 A | 1/1999 | Kojima | 356/328 |
| 6,396,582 B1 | 5/2002 | Buck et al. | 356/328 |
| 6,909,248 B2 | 6/2005 | Clark | 315/291 |
| 2008/0136356 A1* | 6/2008 | Zampini et al. | 315/308 |

OTHER PUBLICATIONS

International Search Report, mailed Mar. 7, 2011, for PCT/US 10/62583, 8 pages.

* cited by examiner

*Primary Examiner* — David H Vu
(74) *Attorney, Agent, or Firm* — Seed IP Law Group PLLC (57) ABSTRACT

A hollow cathode lamp is described with an end cap, an anode, and a cathode. A data storage device is part of the end cap and communicates data to and from a computing device. The data communicated with the computing device may include identification information and usage information corresponding to the hollow cathode lamp. Additionally, a method is described that includes activating a power supply to a hollow cathode lamp and communicating data with a memory device located in the hollow cathode lamp. The data communicated with the memory device includes usage information about an amount of time the hollow cathode lamp has been in use.

20 Claims, 5 Drawing Sheets

HOLLOW CATHODE LAMP ELAPSED TIME RECORDING SYSTEM

BACKGROUND

1. Technical Field

The present disclosure relates to an apparatus, system, and method for monitoring and updating usage information for hollow cathode lamps.

2. Description of the Related Art

A hollow cathode lamp ("HCL") may be used in an atomic absorption spectrometer to emit a narrow spectral line to identify and measure various characteristics of a chemical substance. For example, the concentration of a particular metal in a chemical substance may be determined if the HCL emits a spectral line that matches the spectral line of the particular metal under investigation.

When the HCL is turned on, photons are emitted from the HCL and focused into the chemical substance. Because the photons emitted have a specific spectral line density corresponding to a particular metal, they interact with the particular metal in the chemical substance and some of the photons are absorbed. Based on an amount of photons absorbed in the chemical substance, a determination may be made as to the concentration of the particular metal under investigation. HCLs may also be used as frequency tuners for various light sources, such as lasers.

BRIEF SUMMARY

This summary is provided merely to introduce certain concepts and not to identify any key or essential features of the claimed subject matter.

According to various aspects of the present disclosure, there is described a hollow cathode lamp including an end cap with a data storage device. The data storage device is capable of storing and sending data. The data may include identification information and metric data information about the hollow cathode lamp.

According to other various aspects of the present disclosure, there is a method for communicating data to and from a hollow cathode lamp. The data communicated may be identification information and metric data information about the hollow cathode lamp.

DETAILED DESCRIPTION

In the following description, certain specific details are set forth in order to provide a thorough understanding of various aspects of the invention. However, the invention may be practiced without these specific details.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments of the present disclosure.

In the drawings, similar reference numbers identify similar features or elements. The size and relative positions of features in the drawings are not necessarily drawn to scale.

Figure 1:
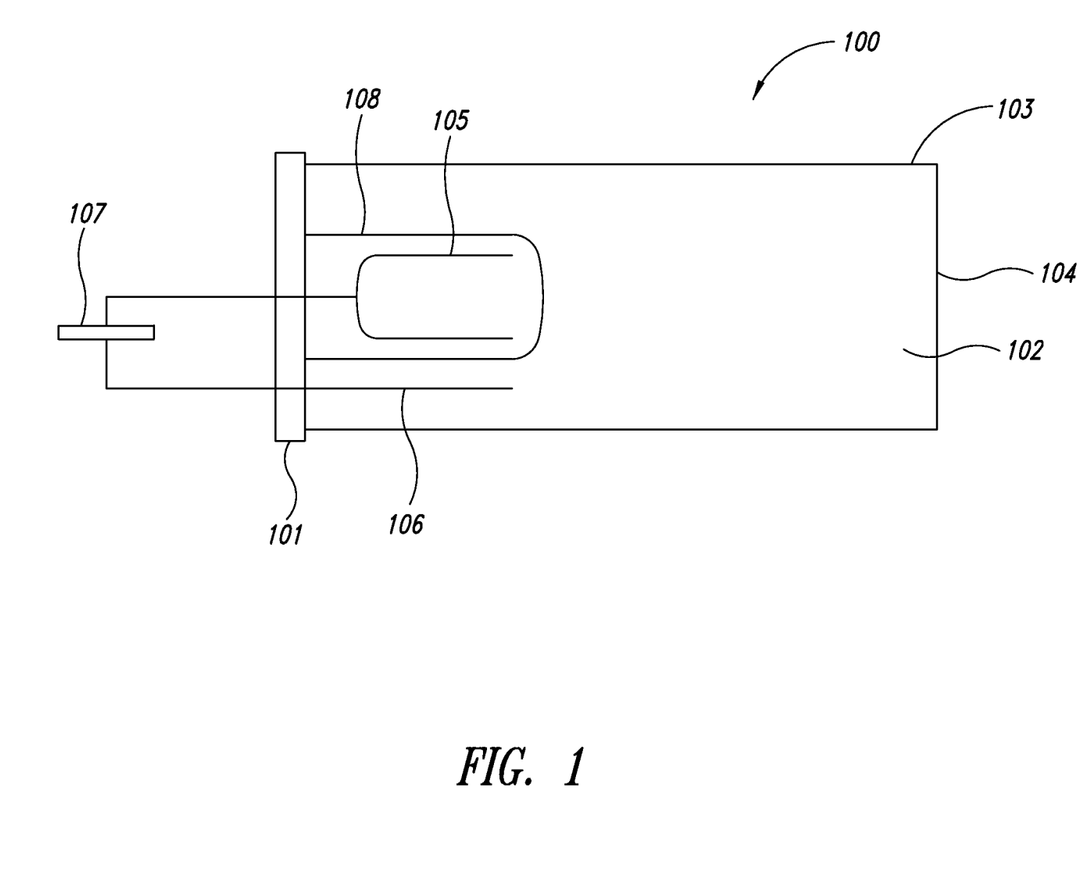
FIG. 1 is a schematic side view of an HCL.

FIG. 1 shows an HCL 100 that has an end cap 101 used to seal an inner environment 102 of a tube 103 connected to the end cap 101. The inner environment 102 may be filled with an inert gas at low pressure, such as argon or neon, and the tube 103 may be made of glass, or other non-reactive material. The HCL 100 also has a tube end 104, opposite the end cap 101, that is transparent to permit photons emitted from a cathode 105 to exit the tube 103.

The cathode 105 emits photons in response to a voltage placed across the cathode 105 and an anode 106. The voltage may be supplied from a direct current voltage source 107 or other power source. The cathode 105 may be housed in a protective casing 108, which may be made of glass or other non-reactive material. The cathode 105 is also made of, or coated in, a metal that the HCL 100 is designed to detect. For example, if the HCL 100 is designed to detect iron, then the cathode 105 will be made of iron or have an iron coating.

During operation of the HCL 100, the anode 106 becomes positively charged and the cathode 105 negatively charged as the voltage from voltage source 107 is applied. The charge difference between the cathode 105 and the anode 106 causes the gas within the inner environment 102 to ionize, or to become a plasma. The ionized particles from the gas are attracted to and bombard the cathode 105 causing atoms from the cathode 105 to sputter off. As the sputtered atoms from the cathode 105 collide with the gas in the inner environment 102, they are excited to higher energy levels. As the sputtered atoms decay from these higher energy levels, photons are emitted through the tube end 104 and into the chemical substance under analysis. The photons emitted due to the decay of the atoms have a unique spectral line density, which enables detection of a particular metal and its characteristics when the photons strike the chemical substance under investigation.

The anode 106 of the HCL 100 has a finite life, thus it is of interest to track and monitor the usage of the HCL 100. One way in which the usage of the HCL 100 can be tracked is with a mercury elapsed time meter. However, because of the toxicity of mercury, a need exists for monitoring usage of the HCL 100 with the use of time meters that do not use mercury. An alternative way to keep track of usage for the HCL 100, without using mercury, is in an external computing device (not shown) that monitors usage information of the HCL 100. For example, the computing device may keep track of when the HCL 100 is turned on and off. The amount of time that power is supplied to the HCL 100 is recorded and logged. The computing device may be accessed at any point to retrieve the usage information for the HCL 100.

Using an external computing device to monitor usage information for the HCL 100 does not account for usage of the HCL 100 in more than one atomic absorption spectrometer, however. Typically, different HCLs, such as the HCL 100, are used interchangeably in different atomic absorption spectrometers. Thus, the computing system may not record an accurate representation of the usage for each HCL, such as the HCL 100. Not knowing the accurate usage of the HCL 100 is undesirable from an operational perspective because the HCL 100 may burnout unexpectedly, or may operate less effectively than a newer HCL.

Figure 2:
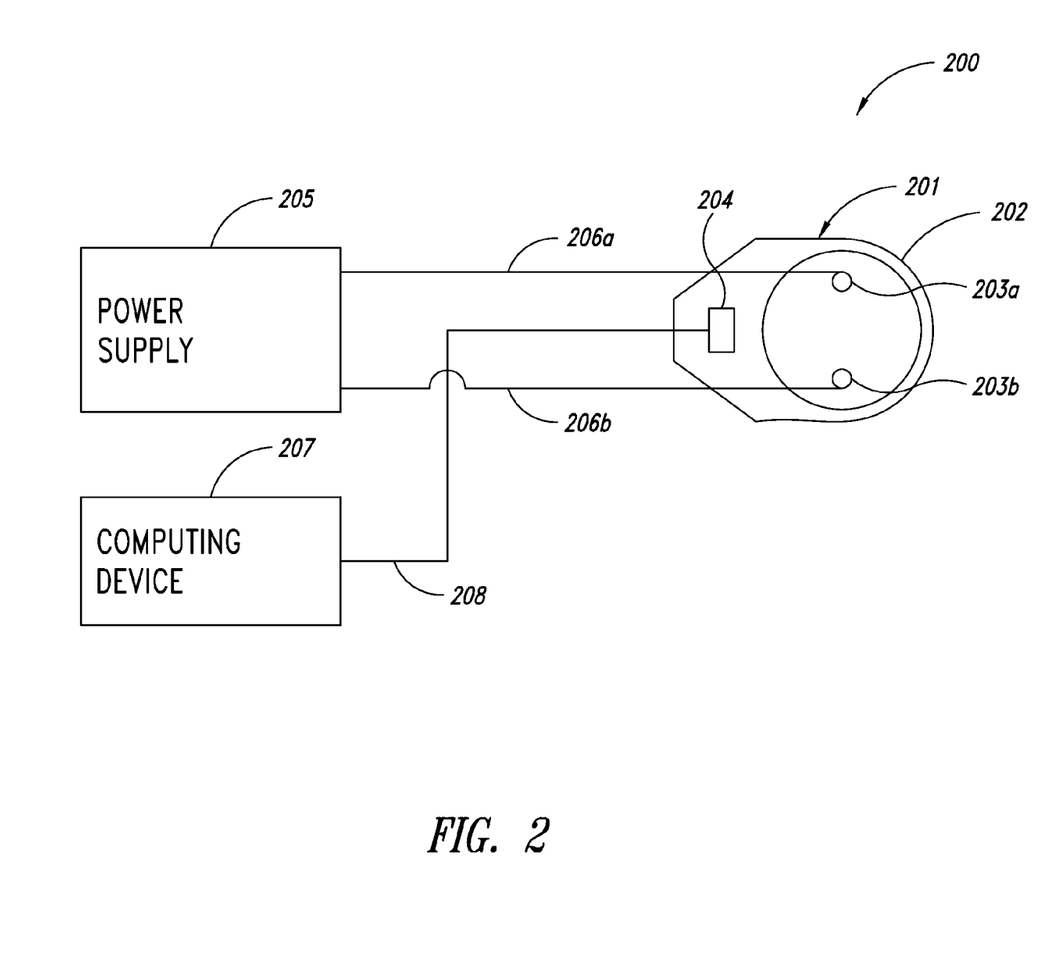
FIG. 2 is a block diagram of an HCL monitoring system according to the present disclosure including the HCL from FIG. 1 as seen looking down upon the HCL's end cap.

According to one embodiment as shown in FIG. 2, an HCL monitoring system 200 causes usage information to be stored in an HCL 201, similar to the HCL 100, so that any atomic absorption spectrometer may access the most up-to-date usage information for the HCL 201. The HCL monitoring system 200 allows the HCL 201 to be used in any compatible atomic absorption spectrometer, which may access and update the usage information for the HCL 201.

The HCL 201 of FIG. 2 has an end cap 202, power supply connections 203a and 203b, and a usage tracking device 204. The connections 203a and 203b are connected to a power supply 205 via connection lines 206a and 206b. The connection lines 206a and 206b are shown as two separate lines that may represent a positive power terminal and a negative power terminal, respectively. The connection lines 206a and 206b may alternatively be implemented in a bus structure or other power connection apparatus that is capable of interfacing with HCL 201.

The usage tracking device 204 is connected to a computing device 207 via a connection line 208. The connection line 208 may be a single signal line with a return path, bus connection, wireless connection, or any other type of connection that facilitates transmission and reception of data between the usage tracking device 204 and the computing device 207. The usage tracking device 204 and the computing device 207 may communicate with one another using any communication protocol that facilitates the exchange of data between two devices.

The usage tracking device 204 is any type of device that can store, update, and communicate information. For example, the usage tracking device 204 may store and communicate identification information and usage information for the HCL 201. The identification information may include a serial number of the HCL 201, an HCL type identifying the type of metal comprising the cathode of the HCL 201, a manufacturer identification of the HCL 201, or the like. In one embodiment, the identification information is permanent so that it cannot be tampered with or changed. The identification information allows the HCL 201 to be properly identified.

According to one embodiment, the usage information stored in the usage tracking device 204 is not permanent and can be communicated between the usage tracking device 204 and the computing device 207. Additionally, the usage information is updated in the computing device 207 and the usage tracking device 204. When the HCL 201 is inserted into an atomic absorption spectrometer, the computing device 207 reads the identification information and the usage information from the usage tracking device 204. The computing device 207 may store both the identification and usage information in an internal memory (not shown) located within the computing device 207. The computing device 207 may also process the identification and usage information to display the current HCL type, the operational state of the HCL 201 (e.g., on, off, usage information, etc.), and other information about the HCL 201 on a display screen to monitor and control the HCL 201 (discussed in more detail below with regard to FIG. 4).

In an additional embodiment, the usage tracking device 204 is an Electrically Erasable Programmable Read-Only Memory ("EEPROM") that may have data read from and written to it by the computing device 207. The usage tracking device 204 may be programmed to store usage information for the HCL 201 in a single memory location, in which case updates of the usage information would continually be overwritten. Alternatively, the usage tracking device 204 may be programmed to store usage information for the HCL 201 as a history log. The history log for the usage information may include a history of the usage for the HCL 201, an identification of the atomic absorption spectrometer the HCL 201 was used in, the date and time for each use of the HCL 201, and any other usage information that is desirable to record, such as current used to power the HCL 201.

Figure 3:
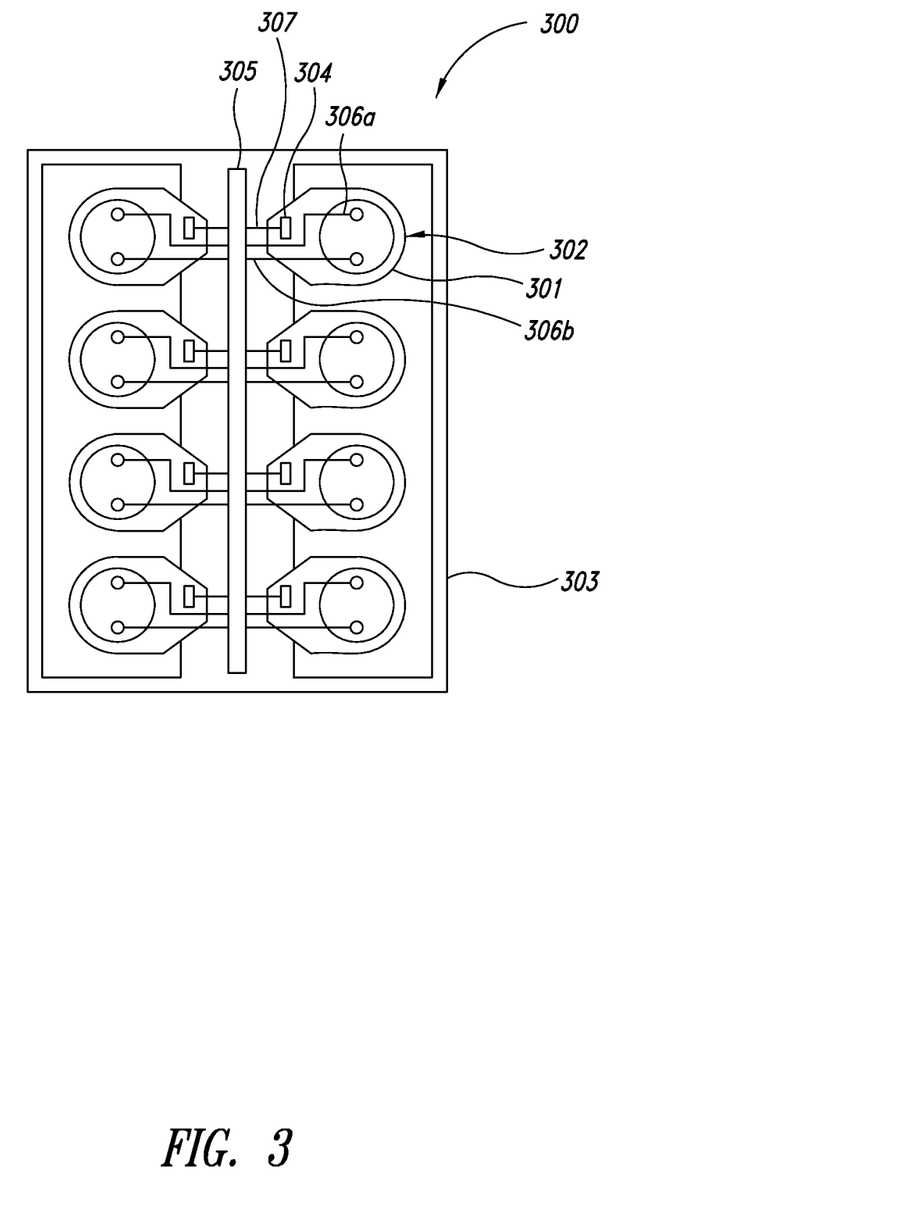
FIG. 3 is an HCL base module capable of housing HCLs and of monitoring according to the HCL monitoring system as shown in FIG. 2.

The HCL 201 may also be part of a larger HCL monitoring system 300 as seen in FIG. 3. Similar to the HCL 201, there are several HCLs, such as the HCL 301, that may be housed in an HCL base module 303. The HCL monitoring system 300 may be used in an atomic absorption spectrometer to measure more than one type of metal in a chemical substance being investigated. Each HCL in the HCL base module 303 may be used to identify a particular metal within the chemical substance and various characteristics of the particular metal within the chemical substance.

As with the HCL 201, the HCL 301 has an end cap 302 that includes a usage tracking device 304. The HCL 301 is connected to a power supply through power lines 306a and 306b. The usage tracking device 304 is connected to a computing device (not shown in FIG. 3, but similar to computing device 207 of FIG. 2) through connection line 307. The power lines 306a and 306b, as well as the connection line 307 may be coupled to a bus 305 that is connected to the computing device (not shown) associated with the atomic absorption spectrometer housing the HCL base module 303.

As further seen in FIG. 3, the HCL base module 303 may hold up to eight HCLs that may be similar to the HCL 301 or an HCL without the usage tracking device 304. The HCL base module 303 may also be configured to hold more or less HCLs depending on the requirements or design of the atomic absorption spectrometer associated with the HCL base module 303.

While FIG. 3 shows the power lines 306a and 306b and the connection line 307 extending outside the end cap 302 for coupling to the bus 305, each line 306a, 306b, and 307 may alternatively be embedded in the end cap 302 and exit a part of the end cap 302, such as the underside of the end cap 302, for connection to the HCL base module 303. By way of example, the lines 306a, 306b, and 307 may be bundled together in a plug (not shown) or other device, which is capable of mating with a matching receptacle (not shown) on the HCL base module 303.

In operation, the HCL base module 303 couples each of the inserted HCLs, such as the HCL 301, to the atomic absorption spectrometer and the associated computing device (not shown). The computing device controls each of the HCLs in the HCL base module 303 and monitors the usage of each HCL. According to an aspect of the disclosure, the usage information for the HCL 301 is maintained in the usage tracking device 304. The usage information may include metric data about the amount of time the HCL 301 has been in use, the current supplied to the HCL 301 for any given use, which atomic absorption spectrometer the HCL 301 was used in for any give use, etc. But because each HCL in the HCL base module 303 may have different operating requirements and have been used previously in a different atomic absorption spectrometer, the currently used atomic absorption spectrometer may need to obtain identification information and usage information for each HCL prior to and during use.

Figure 4:
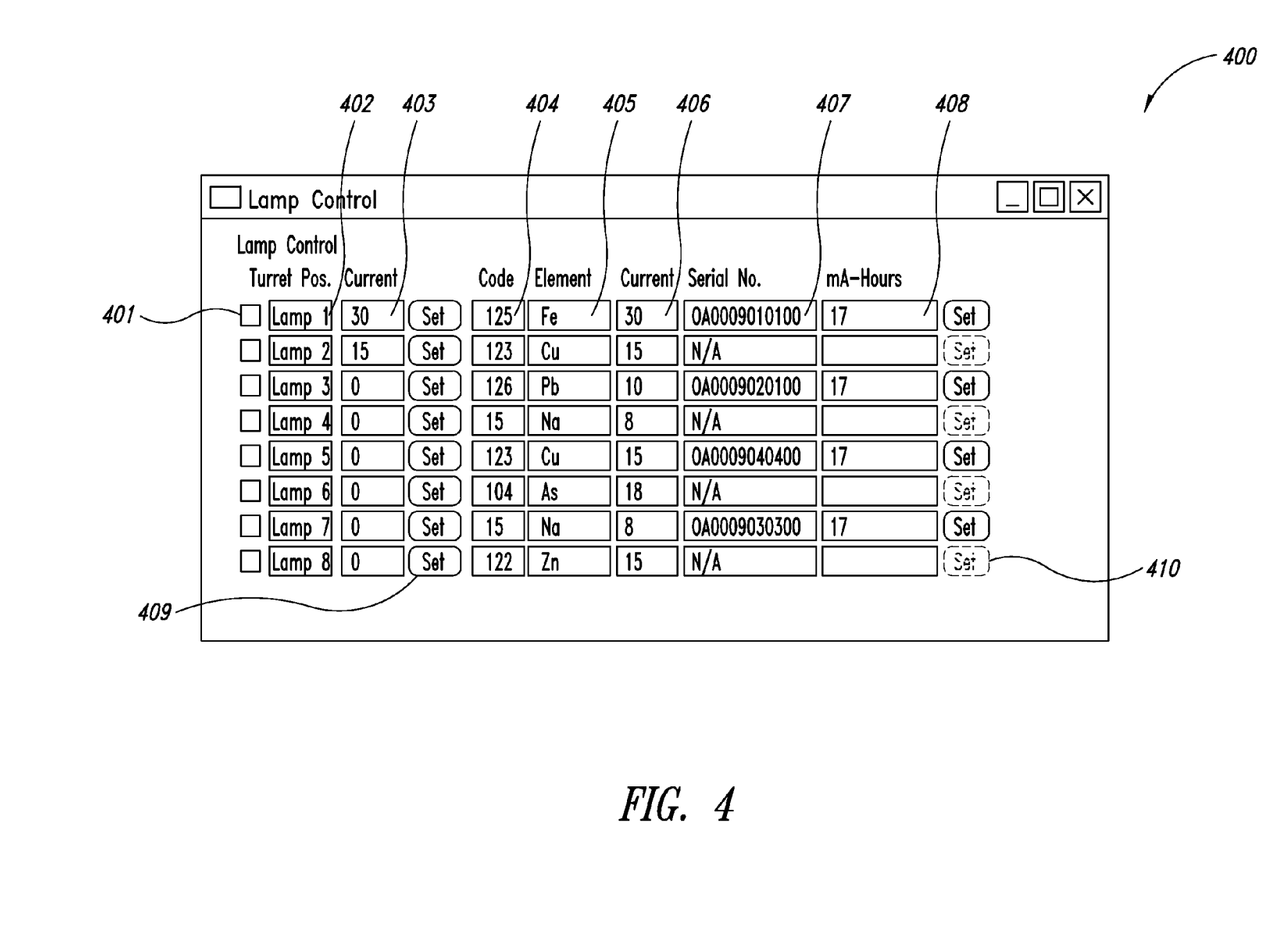
FIG. 4 is a screen shot of a lamp control display used to monitor and control the HCLs in the HCL base module as shown in FIG. 3.

A lamp control display 400 is shown in FIG. 4, according to one embodiment, for monitoring and controlling usage of each HCL inserted in the HCL base module 303. The lamp control display 400 may be controlled by the computing device (not shown) controlling the HCLs in the HCL base module 303, similar to computing device 207 as seen in FIG. 2. Alternatively, the lamp control display 400 may be controlled by a separate computing device (not shown) in communication with the computing device controlling the HCLs. The separate computing device communicating with the computing device controlling the HCLs may retrieve information and display it on the lamp control display 400.

The lamp control display 400 has a lamp selection box 401, a lamp position box 402, and a current setting box 403. The lamp selection box 401 is used to select a corresponding HCL for monitoring and controlling. The lamp position box 402 identifies the physical position of the corresponding HCL in the HCL base module 303. The current setting box 403 is used to display an operating current for the corresponding HCL that may be set using a button 409.

For each HCL identified on the lamp control display 400, there is also a code identification box 404 identifying a corresponding type of HCL, as well as an element box 405 indicating the type of metal the corresponding HCL can identify (i.e., what type of cathode is in the corresponding HCL). The lamp control display 400 also has a second current box 406 that is used to show a preferred operating current for use with the corresponding HCL. There is also a serial number identification box 407 used to identify the HCL by serial number. The lamp control display 400 has a time usage box 408 for indicating the total elapsed time the corresponding HCL has been in use, which may be communicated and stored in the usage tracking device 304 when a time usage set button 410 is selected. The information in the time usage box 408 may also be communicated and stored in the usage tracking device 304 without the time usage set button 410 being selected.

According to one embodiment, the usage information for a given HCL as indicated in the time usage box 408 is measured in units of current multiplied by time, such as milliamp-hours (mA-hours). A benefit to measuring the usage information for a given HCL in mA-hours is to provide a consistent unit of measurement of an HCL that incorporates the current used. Alternatively, any measurement of time, or time-related measurement, may be used as long as the unit of measurement gives an accurate indication of current usage of the given HCL, including usage from other atomic absorption spectrometers.

By way of example, as seen in FIG. 4, if the HCL at position Lamp 1 (as labeled in the lamp position box 402) is used in the atomic absorption spectrometer associated with the lamp control display 400 and is run for 34 minutes at 30 milliamps, a usage time as displayed in the time usage box 408 is 17 mA-hours (i.e., 1020 mA-minutes) and will be recorded in the usage tracking device of the HCL at position Lamp 1. If the actual time (i.e., 34 minutes) was recorded instead of 17 mA-hours, then there would be no indication as to what operating current was supplied to the HCL at position Lamp 1 for 34 minutes. An HCL running at a higher current than 30 mA for 34 minutes will use more life of the HCL than an HCL running at 30 mA for 34 minutes. Thus, it is preferred that the time usage information be recorded in units of current multiplied by time. Even so, HCL usage may be recorded in units of time alone if a record of the current used for the HCL at position Lamp 1 is also recorded or known.

As further shown in FIG. 4, there is a sodium (Na) HCL at position Lamp 4 as indicated by the element box 405 for position Lamp 4. The sodium HCL at position Lamp 4 does not have an associated serial number, which is indicated by the "N/A" in the serial number identification box 407 for the HCL at position Lamp 4. When identification information for an HCL is not read from the HCL, as described above with regard to the usage tracking devices 204 and 304, or if there is no identification information in the HCL, then the serial number identification box 407 may remain empty or display "N/A." Similarly, when there is no usage information stored in the HCL or if it is not accessible, then the time usage box 408 may be empty, such as with the HCL at position Lamp 4.

As further shown in FIG. 4, when an HCL, such as the lead (Pb) HCL at position Lamp 3, is inserted into the atomic absorption spectrometer the identification and usage information may be read from the HCL at position Lamp 3. The various boxes and fields corresponding to position Lamp 3 are populated with the identification and usage information. Unlike the HCL at position Lamp 4, however, the HCL at position Lamp 3 has a serial number as shown in the serial identification box 407 at position Lamp 3. The time usage box 408 at position Lamp 3 is also populated with a usage value from the corresponding HCL. The usage value populated into the time usage box 408 at position Lamp 3 may be an initial usage value corresponding to past usage of the HCL at position Lamp 3. Any subsequent usage of the HCL at position Lamp 3 will be added to the usage value displayed in the time usage box 408 and stored in the usage tracking device of the HCL at position Lamp 3.

Figure 5:
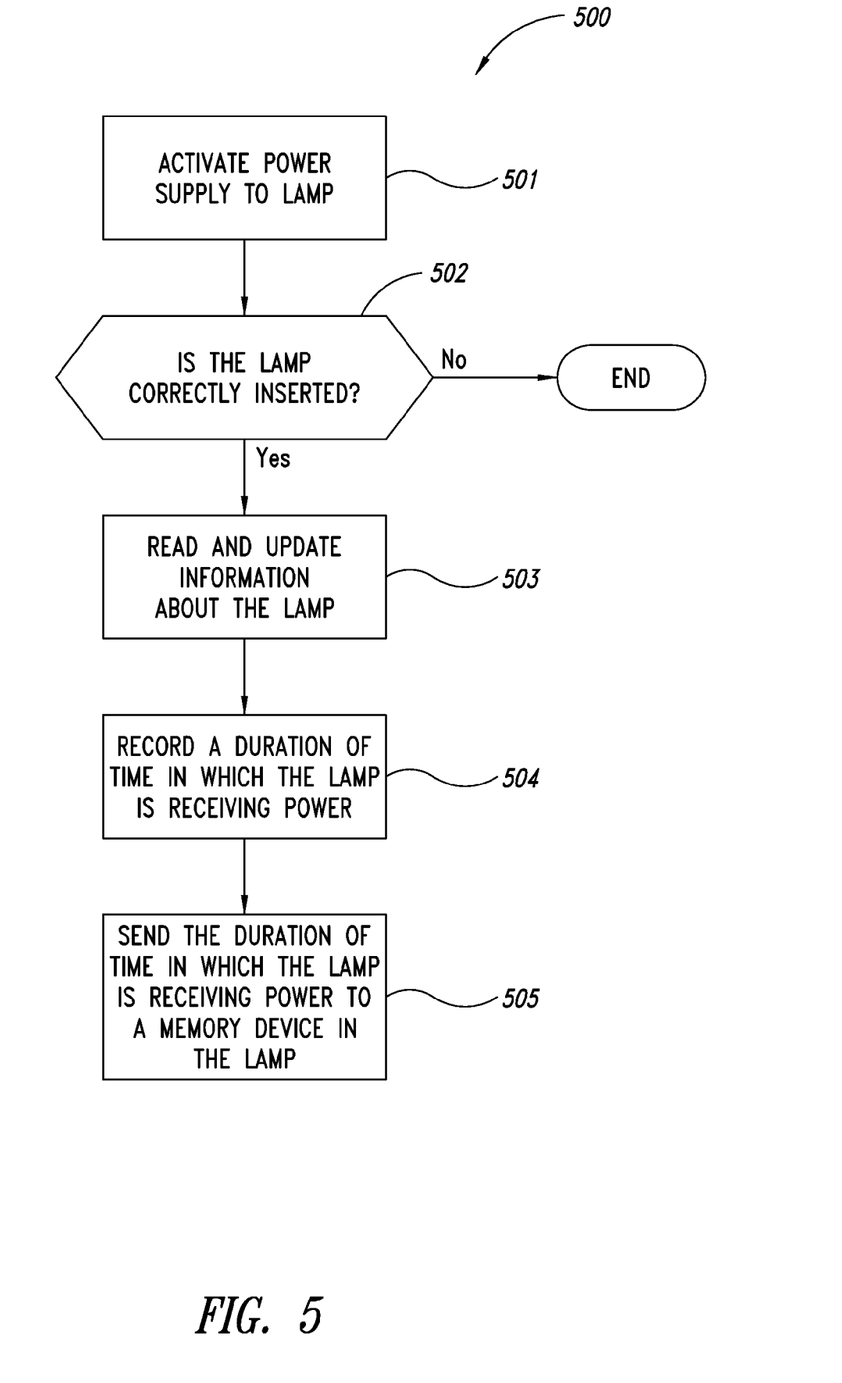
FIG. 5 is a flowchart describing a method of monitoring HCLs according to the present disclosure.

A more detailed description of monitoring and updating the usage information for an HCL, such as the HCL 301, is shown in a process 500 of FIG. 5. At the beginning of the process 500, the power supply to the HCL 301 is activated at step 501. At step 502 it is determined if the HCL 301 is correctly inserted into the HCL base module 303. If the HCL 301 is not correctly inserted, then the process ends because the HCL 301 cannot be operated. If the HCL 301 is correctly inserted, then the identification and usage information are read from the usage tracking device 304 at step 503.

In one embodiment, the power supply to the HCL 301 is activated at step 501 for the purpose of reading and writing information to the usage tracking device 304, as well as for operating the HCL 301. In an alternative embodiment, when the power supply is activated at step 501, only the identification and usage information are read at step 503, but there is not enough power supplied to operate the HCL 301. Only when the HCL 301 is operated will operating power be supplied. Reading only the information stored in the usage tracking device 304 of the HCL 301 at step 501 without supplying operating power may increase the life of the HCL 301. Alternatively, only operating power is supplied to the HCL 301 at step 501, thus there is no need to control two different types of power supplies.

As further shown in FIG. 5, at step 504, a duration of lamp usage is determined based on a difference between a time at which the HCL 301 was activated and a time when the HCL 301 was deactivated. In one aspect, the difference in time may be determined by a timer and continuously updated and displayed in the time usage box 408 of the lamp control display 400. The difference in time between the activation time and the deactivation time may alternatively be added to any already stored usage information in the usage tracking device 304 as displayed in the time usage box 408. The HCL 301 activation stop time may be the actual deactivation of power to the HCL, but alternatively may be a temporary stop time indicating when the time usage set button 410 is selected or when the usage information is automatically updated.

At step 505, the time difference or current time usage as displayed in the time usage box 408 may be updated in the usage tracking device 304 of the HCL 301. In one aspect, updating the usage information in the usage tracking device 304 may be done when the time usage set button 410 is selected. Alternatively, the usage information may be updated in the usage tracking device 304 automatically, for example, at fixed time intervals, or updated when the power supply to the HCL 301 is deactivated.

By way of example, the computing device 207 may update the lamp usage in the usage tracking device 304 every five to ten minutes. Other fixed time intervals are also acceptable as long as they do not interfere with the accuracy of monitoring and updating the lamp usage. Additionally, the fixed time interval may depend on the type of HCL being monitored. If an HCL has a short life expectancy, then the fixed time interval would be shorter than for an HCL with a longer life expectancy.

In an another embodiment, instead of periodically updating the lamp usage at fixed intervals, the computing device 207 may start a timer when the power supply to the lamp is activated and end the timer when the power supply to the lamp is deactivated to only update the lamp usage once. The difference between the start time and end time may be used to determine a total lamp usage corresponding to the duration of power activation and may be stored in the computing device 207, sent to the usage tracking device 304, or both. Once the usage information is recorded and the power to the HCL 301 is deactivated, the HCL 301 may be removed from the HCL base module 303 for use in a different atomic absorption spectrometer, or continued for later use in the current atomic absorption spectrometer with an accurate recordation of current usage for the HCL 301.

The various aspects of the disclosure described above may be combined even if not described in such a way. Additionally, in general, in the following claims, the terms used should not be construed to limit the claims to specific aspects of the disclosure described in the specification, but should be construed to include all possible aspects along with the full scope of equivalents to which such claims are entitled. Accordingly, the claims are not limited by the disclosure.

The invention claimed is:

1. A hollow cathode lamp, comprising:
an end cap;
an enclosure sealed at one end by the end cap
an anode and a cathode housed in the enclosure;
a plurality of connection terminals coupled to the end cap; and
a data storage device coupled to the end cap and to at least one of the plurality of connection terminals, the data storage device capable of sending informational data to a computing device and storing usage data received from the computing device.

2. The hollow cathode lamp of claim 1, wherein the plurality of connection terminals includes a data communication connection and a power supply connection.

3. The hollow cathode lamp of claim 1, wherein the informational data includes a type of the hollow cathode lamp and the usage data includes metric data.

4. The hollow cathode lamp of claim 3, wherein the metric data includes an amount of time the hollow cathode lamp has been in use.

5. The hollow cathode lamp of claim 4, wherein the amount of time the hollow cathode lamp has been in use is measured in units of current multiplied by time.

6. The hollow cathode lamp of claim 3, wherein the metric data is updated at a fixed time interval during use of the hollow cathode lamp.

7. The hollow cathode lamp of claim 1, wherein the data storage device is an Electrical Erasable Programmable Read-Only Memory (EEPROM).

8. The hollow cathode lamp of claim 3, wherein the metric data is produced and monitored by the computing device.

9. A hollow cathode lamp containment system, comprising:
a control base module;
one or more hollow cathode lamps coupled to the control base module, each of the one or more hollow cathode lamps including: (a) an end cap, (b) an enclosure sealed at one end by the end cap; (c) an anode and a cathode housed in the enclosure; and (d) a plurality of connection terminals coupled to the end cap; and
one or more memory storage sections coupled to the one or more hollow cathode lamps, the one or more memory storage sections capable of communicating data including a type of a respective hollow cathode lamp and hollow cathode lamp metric data.

10. The system of claim 9, wherein the data is communicated to a computing device that is located at a separate location from the one or more memory storage sections.

11. The system of claim 9, wherein the one or more memory storage sections are located in one or more end caps of the one or more hollow cathode lamps.

12. The system of claim 9, wherein the data storage device is an Electrical Erasable Programmable Read-Only Memory (EEPROM).

13. The system of claim 9, wherein the hollow cathode lamp metric data includes an amount of time a respective hollow cathode lamp has been in use.

14. A method comprising:
activating a power supply to at least one hollow cathode lamp, wherein the at least one hollow cathode lamp includes: (a) an end cap, (b) an enclosure sealed at one end by the end cap; (c) an anode and a cathode housed in the enclosure; and (d) a plurality of connection terminals coupled to the end cap; and
communicating data stored in a memory device located in the at least one hollow cathode lamp to a computing device, the data including usage information corresponding to an amount of time the at least one hollow cathode lamp has been used.

15. The method of claim 14, further comprising:
determining at fixed intervals of time that the at least one hollow cathode lamp is correctly inserted into an analyzer; and
causing a display to be generated that lists the at least one hollow cathode lamp and the usage information.

16. The method of claim 15, wherein the display further lists a type of the at least one hollow cathode lamp and a current that flows into the at least one hollow cathode lamp.

17. The method of claim 14, wherein the memory device is an Electrical Erasable Programmable Read-Only Memory (EEPROM).

18. The method of claim 14, wherein the usage information is measured in a unit of current multiplied by time.

19. The method of claim 14, wherein the usage information is produced and monitored by the computing device and stored in the memory device located in the at least one hollow cathode lamp.

20. The method of claim 14, further comprising:
transmitting the usage information to the memory device at fixed intervals of time.

* * * * *